US00PP08283P

United States Patent [19]

Kientzler

[11] Patent Number: Plant 8,283

[45] Date of Patent: Jun. 29, 1993

[54] IMPATIENS PLANT NAMED ANTIGUA

[75] Inventor: Ludwig Kientzler, Gensingen, Fed. Rep. of Germany

[73] Assignee: Paul Ecke Ranch, Inc., Encinitas, Calif.

[21] Appl. No.: 872,417

[22] Filed: Apr. 23, 1992

[51] Int. Cl.[5] ..... A01H 5/00

[52] U.S. Cl. ..... Plt./87.6

[58] Field of Search ..... Plt./87.6

*Primary Examiner*—James R. Feyrer

*Assistant Examiner*—Erich Veitenheimer

*Attorney, Agent, or Firm*—Foley & Lardner

[57] ABSTRACT

A new and distinct cultivar of Impatiens plant named Antigua, characterized by its large, bright dark orange flowers, compact growth habit with excellent self-branching without pinching, medium green, non-variegated foliage with reddish midveins, very early and uniform flowering, floriferous habit, and by its suitability to pot or hanging basket culture.

1 Drawing Sheet

The present invention relates to a new and distinct cultivar of plant known as Impatiens and commercially known as New Guinea Impatiens. The new cultivar is known by the cultivar name Antigua, and was developed by the inventor Ludwig Kientzler in Gensingen, Federal Republic of Germany by crossing the cultivar designated D-367 (seed parent) with the cultivar designated 85-17-04 (pollen parent).

Asexual reproduction by terminal (stem tip) cuttings taken by me or under my supervision at Gensingen, Federal Republic of Germany has shown that the unique features of this new impatiens are stabilized and are reproduced true to type in successive propagations.

The following characteristics distinguish the new impatiens from both its parent varieties and other cultivars of this general type known and used in the floriculture industry:

1. Compact growth habit, yet excellent self-branching to produce full and well formed plants. Plants in 16.5 cm pots were 15 cm tall and 25 cm wide, eight weeks after planting.

2. Large, bright dark orange flowers. Open flowers measure up to 6.5 cm in diameter.

3. Early flowering and very floriferous. Plants in 16.5 cm pots were in flower 7 weeks after planting.

4. Medium green non-variegated foliage with reddish midveins. Nice color contrast between flowers and foliage.

5. Well suited both to 4" pot and 8" hanging basket culture.

The flower color of Antigua is similar to Aurore (U.S. Plant Pat. No. 6,685), Marumba (U.S. Plant Pat. No. 7,372), and Epia, disclosed in my pending application. However, all of these cultivars have either bronzed or variegated foliage, while Antigua does not. Moreover, the flower size of Antigua is larger and flowering is much earlier.

The accompanying color photograph is a top perspective view of the new cultivar, showing color as true as it is reasably possible to obtain in a colored reproduction of this type.

The following is a detailed description of my new impatiens cultivar based on plants grown under commercial practice in Encinitas, Calif. Plants were started as rooted cuttings and were transplated in mid-December into 16.5 cm (6.5 inch) pots, one pot per plant. By mid-February, plants were growing vigorously and were in flower. The values, measurements and observations noted below were taken from plants in full bloom in mid-February.

Color references are made to the Royal Horticultural Society Colour Chart (RHS), except where general terms of ordinary dictionary significance are used.

Parentage: Cross between D-367 (seed) and 85-17-04 (pollen).

Asexual reproduction:

A. *Cutting type.*—Tip, with stems 2–3 cm long developing to 4–5 cm after 21 days in propagation.

B. *Time to initiate roots.*—8–10 days at 23° C.; nicely developed root mass in 18–21 days.

C. *Rooting habit.*—Numerous, fibrous, adventitious roots from the stem.

Plant description:

A. *Form.*—Symmetrical, bush shaped, flowering herb, with self-branching characteristics giving the plant a full appearance. Pinching is not recommended since it does not enhance branching and only delays flowering by removing flower buds.

B. *Habit of growth.*—Vigorous, self-branching habit, producing whorls of leaves and flowers. Growth is indeterminate and flowering is continuous.

C. *Foliage description.*—Leaves are simple. Lower leaves on stems are opposite. Higher leaves in whorls of 3–5, but predominately 5. 1. Leaf shape: Broadly lanceolate to ovate. Leaf blade tips are acuminate; bases acute to attenuate. 2. Leaf blade size: Mature leaves 12–13 cm long and approximately 4.5 cm wide. 3. Petiole length: Approximately 2 cm. 4. Leaf margin: Lightly ciliated and finely serrated. 5. Leaf texture: Slightly rugose. a. Upper surface: Glabrous. b. Under surface: Glabrous. 6. Leaf color: Medium green with reddish midvein on proximal end of leaf blade. a. Upper surface: Mature leaves near 147/A; immature leaves lighter than 147a. b. Under surface: Greyed green, between 191A and 191B, with reddish veins. 7. Venation: Pinnate.

Flowering description:

A. *Flowering habits.*—Very floriferous. Flowering is continuous. Flowers develop progressively around the whorl of leaves, taking 5–7 days from buds which show color, to bloom. Flowers are single and large, lasting for 2–3 weeks.

B. *Natural flowering season.*—Flowering is indeterminate and occurs throughout the year. Quantity of flowers increases with increasing light intensity and duration. However, floriferousness may wane during hot summer days in temperate climates.

C. *Flower buds.*—Ellipsoidal and covered with 3 sepals plus 2 rudimentary sepals fused into the under surface of the superior petal. A spur originates from the base of the inferior sepal. Spur is red and approximately 5.5 cm long.

D. *Flowers borne.*—Singly, on reddish pedicels approximately 6–7 cm long.

E. *Quantity of flowers.*—One flower per leaf. Flowers occur progressively around the whorl of leaves so that tight buds to mature flowers are visible at the same time.

F. *Petals.*—Petals open nearly perpendicular to the pedicel so the plane of the flower surface is nearly flat. 1. Number of petals: Five (5) petals, all overlapping. 2. Shape: All petals are heart-shaped. Superior petal has a broad base. Other petals have a pointed base. 3. Dark Orange. a. Upper surface: Darker and brighter than 33A. b. Under surface: Near 33A. 4. Flower size: Approximately 6.5 cm in diameter.

G. *Reproductive organs.*—Flowers are monoecious. 1. Stamens: Five (5), broad and fused to form a tube around the ovary, tinged with red. 2. Anther: Hooded and cream colored. 3. Pollen: Cream colored. 4. Stigma: Five pointed star, colorless. 5. Styles: Very short. 6. Ovary: 5-celled, 4–5 cm long until fertilized. Grows to 1 cm or longer after fertilization; green.

Resistance to disease: Good resistance to common stem and root disease, Rhizoctonia and Pythium. Botrytis may be a problem in humid or mist propagation environments, but no greater than with other New Guinea Impatiens cultivars.

I claim:

1. A new and distinct cultivar if Impatiens plant named Antigua, as illustrated and described.

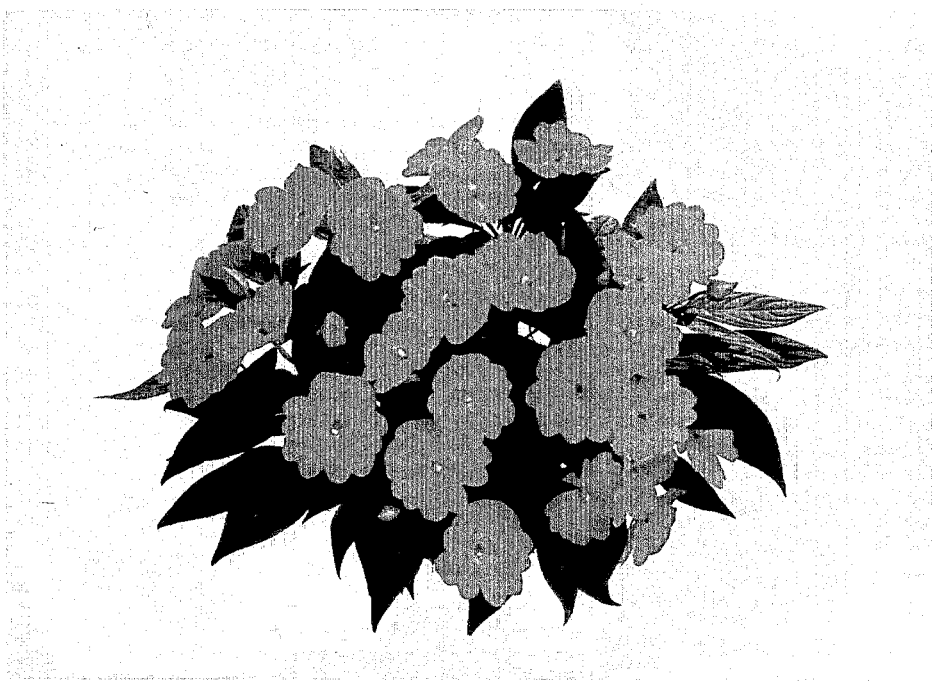

* * * * *